(12) United States Patent
Ko (10) Patent No.: US 9,821,171 B2
(45) Date of Patent: Nov. 21, 2017

(54) OPTICAL APPARATUS FOR SKIN TREATMENT, METHOD FOR CONTROLLING THE OPTICAL APPARATUS, AND METHOD FOR SKIN TREATMENT

(75) Inventor: Kwang Chon Ko, Gyeonggi-do (KR)

(73) Assignee: Lutronic Corporation, Gyeonggi-do (KR)

( * ) Notice: Subject to any disclaimer, the term of this patent is extended or adjusted under 35 U.S.C. 154(b) by 262 days.

(21) Appl. No.: 13/885,541

(22) PCT Filed: Nov. 14, 2011

(86) PCT No.: PCT/KR2011/008655
§ 371 (c)(1),
(2), (4) Date: May 15, 2013

(87) PCT Pub. No.: WO2012/067384
PCT Pub. Date: May 24, 2012

(65) Prior Publication Data
US 2013/0268031 A1    Oct. 10, 2013

(30) Foreign Application Priority Data

Nov. 15, 2010   (KR) .......................... 10-2010-0113386

(51) Int. Cl.
*A61B 18/20*    (2006.01)
*A61B 18/22*    (2006.01)
(Continued)

(52) U.S. Cl.
CPC ............ *A61N 5/0616* (2013.01); *A61B 18/20* (2013.01); *A61B 18/203* (2013.01);
(Continued)

(58) Field of Classification Search
None
See application file for complete search history.

(56) References Cited

U.S. PATENT DOCUMENTS 5,554,172 A * 9/1996 Horner ............... A61B 18/1402
606/22
5,814,040 A * 9/1998 Nelson ................. A61B 18/203
128/898
(Continued)

FOREIGN PATENT DOCUMENTS

JP    2002-272861 A    9/2002
JP    2003-164534 A    6/2003
(Continued)

OTHER PUBLICATIONS

Aguilar et al., Cryogen Spray Cooling Efficiency: Improvement of Port Wine Stain Laser Therapy Through Multiple-Intermittent Cryogen Spurts and Laser Pulses, Lasers in Surgery and Medicine 31:27-35 (2002).*

(Continued)

*Primary Examiner* — Lynsey Eiseman
*Assistant Examiner* — Manolis Pahakis
(74) *Attorney, Agent, or Firm* — Osha Liang LLP (57) ABSTRACT

The present invention relates to an optical apparatus for skin treatment and to a method for controlling the optical apparatus. The optical apparatus includes a radiating part for radiating light generated in a light-generation part onto a target position of the skin, a cooling part for spraying cooling gas onto the target position to cool the surface of the skin, and a control part for controlling operations of the radiating part and cooling part. The control part controls the radiating part and the cooling part such that the radiating part radiates a first light onto the target position, the cooling part sprays the cooling gas onto the target position, and then the radiating part radiates a second light onto the target position.

12 Claims, 7 Drawing Sheets

(51) Int. Cl.
*A61N 5/06* (2006.01)
*A61N 5/067* (2006.01)
*A61B 18/00* (2006.01)
*A61N 5/00* (2006.01)

(52) U.S. Cl.
CPC ............... *A61B 2018/00017* (2013.01); *A61B 2018/00452* (2013.01); *A61N 2005/007* (2013.01); *A61N 2005/0644* (2013.01)

(56) References Cited

U.S. PATENT DOCUMENTS

| | | | | |
|---|---|---|---|---|
| 5,820,626 | A * | 10/1998 | Baumgardner | 606/13 |
| 5,964,749 | A * | 10/1999 | Eckhouse | A61B 18/203 606/9 |
| 6,162,210 | A * | 12/2000 | Shadduck | A61B 18/02 606/20 |
| 6,168,589 | B1 * | 1/2001 | Tobinick | A61B 18/203 606/10 |
| 6,190,377 | B1 * | 2/2001 | Kuzdrall | A61B 18/203 606/10 |
| 6,248,103 | B1 * | 6/2001 | Tannenbaum | A61B 18/0218 128/898 |
| 6,413,253 | B1 * | 7/2002 | Koop et al. | 606/27 |
| 6,585,725 | B1 * | 7/2003 | Mukai | 606/10 |
| 6,595,985 | B1 * | 7/2003 | Tobinick | A61B 18/203 606/13 |
| 6,607,524 | B1 * | 8/2003 | LaBudde | A61C 1/0046 604/20 |
| 6,682,524 | B1 * | 1/2004 | Elbrecht et al. | 606/9 |
| 7,780,656 | B2 * | 8/2010 | Tankovich | 606/20 |
| 7,824,395 | B2 * | 11/2010 | Chan | A61B 18/203 128/898 |
| 8,290,006 | B1 * | 10/2012 | Gradl et al. | 372/29.014 |
| 2001/0009997 | A1 * | 7/2001 | Pope | A61B 18/203 606/9 |
| 2001/0029364 | A1 * | 10/2001 | Almeida | A61B 18/203 606/9 |
| 2001/0041886 | A1 * | 11/2001 | Durkin et al. | 606/9 |
| 2002/0095143 | A1 * | 7/2002 | Key | 606/9 |
| 2002/0138072 | A1 * | 9/2002 | Black et al. | 606/10 |
| 2003/0065313 | A1 * | 4/2003 | Koop et al. | 606/9 |
| 2003/0065314 | A1 | 4/2003 | Altshuler et al. | |
| 2004/0162596 | A1 * | 8/2004 | Altshuler et al. | 607/88 |
| 2005/0137658 | A1 * | 6/2005 | Hennings | A61B 18/203 607/96 |
| 2007/0088408 | A1 * | 4/2007 | Amornsiripanitch | A61B 18/203 607/88 |
| 2007/0191821 | A1 * | 8/2007 | Boxer Wachler | A61B 18/20 606/9 |
| 2009/0030407 | A1 * | 1/2009 | Verkruysee et al. | A61B 18/20 606/9 |
| 2011/0060322 | A1 * | 3/2011 | Manstein | 606/9 |
| 2011/0137303 | A1 * | 6/2011 | Dolleris et al. | 606/17 |
| 2011/0313408 | A1 * | 12/2011 | Tankovich et al. | 606/3 |
| 2012/0065551 | A1 * | 3/2012 | Aviad et al. | 601/2 |

FOREIGN PATENT DOCUMENTS

| | | | |
|---|---|---|---|
| JP | 2003164534 A | * | 6/2003 |
| JP | 2009-101183 A | | 5/2009 |

OTHER PUBLICATIONS

Sturesson et al., Mathematical modelling of dynamic cooling and pre-heating, used to increase the depth of selective damage to blood vessels in laser treatment of port wine stains. Phys. Med. Biol. 41 (1996) 413-428.*

Jia et al., Improvement of Port Wine Stain Laser Therapy by Skin Preheating Prior to Cryogen Spray Cooling: A Numerical Simulation, Lasers in Surgery and Medicine 38:155-162 (2006).*

International Search Report issued in PCT/KR2011/008655 dated May 22, 2012 (18 pages).

Written Opinion issued in PCT/KR2011/008655 dated May 22, 2012 (13 pages).

Patent Abstracts of Japan Publication No. 2002-272861 dated Sep. 24, 2002 (1 page).

Patent Abstracts of Japan Publication No. 2003-164534 dated Jun. 10, 2003 (1 page).

Patent Abstracts of Japan Publication No. 2009-101183 dated May 14, 2009 (1 page).

* cited by examiner

OPTICAL APPARATUS FOR SKIN TREATMENT, METHOD FOR CONTROLLING THE OPTICAL APPARATUS, AND METHOD FOR SKIN TREATMENT

TECHNICAL FIELD

The present invention relates to an optical apparatus for skin treatment, a method for controlling the optical apparatus and a method for skin treatment, and in particular, to an optical apparatus for skin treatment, a method for controlling the optical apparatus and a method for skin treatment in which a cooling system using a cooling gas is included.

BACKGROUND ART

In recent years, the technology to treat the skin has been widely applied to methods of changing or removing states of skin tissues by radiating light. Therefore, the optical apparatus for skin treatment is developed using various types of electromagnetic radiations such as a laser beam, a flash lamp, RF frequency, a microwave, an ultrasound and the like.

If the light is radiated using the optical apparatus for skin treatment, the light with a specific wavelength may be penetrated to the inside of the skin, and may be absorbed into the various tissues such as collagen, hair follicles, and hemoglobin located on the inside of the skin according to the wavelength characteristics. In addition, the absorbed light is converted into thermal energy in the tissue to change a state of the tissue by applying thermal damage to the tissue.

At this time, the skin surface is typically cooled before the light is radiated or while the light is radiated, since it may cause damage on the skin surface by the thermal energy generated during radiating the light. For example, the skin is cooled by a refrigerant or heat transfer device in which the skin is in contacted with a thermal conductivity member to maintain a low temperature, or a method for cooling the skin is mainly used in which the cooling gas of an extremely low temperature is sprayed onto the skin surface. Thus, the treatment of the internal tissue of the skin is achieved in a state where the surface of the skin is maintained at the low temperature when the light is radiated.

However, if the treatment is processed in a state where the skin surface is cooled as in the prior art, there is a problem in that it may cause damage on the skin surface when the light is radiated as output of more than a certain size. Thus, there was a limit to process the treatment by supplying the sufficient thermal energy to the skin tissue.

Furthermore, when the treatment of removing a capillary vessel located on the skin surface is performed, if the skin surface is cooled as in the prior art, a phenomenon that the capillary vessel is contracted and disappeared from the skin surface can be observed. As such, in a case of some lesions, when the skin surface is cooled, since the temperature of skin surface is rapidly decreased and the lesion is temporarily disappeared, there is a problem difficult to treat by radiating the light onto the correct location after cooling the skin.

DISCLOSURE

Technical Problem

In order to solve the above problems, the present invention is to provide an optical apparatus for skin treatment and a method for controlling the optical apparatus in which sufficient thermal energy can be provided to an internal tissue of the skin without being damaged to the skin.

In addition, the present invention is to provide an optical apparatus for skin treatment and a method for controlling the optical apparatus in which a lesion temporarily disappeared due to the reduction of the temperature of the skin may be minimized.

Technical Solution

The object of the present invention can be achieved by an optical apparatus for skin treatment, including: a radiating part for radiating light generated in a light-generation part onto a target position of the skin; a cooling part for spraying cooling gas onto the target position to cool the surface of the skin; and a control part for controlling operations of the radiating part and cooling part, wherein the control part controls the radiating part and the cooling part such that the radiating part radiates a first light onto the target position, the cooling part sprays the cooling gas onto the target position, and then the radiating part radiates a second light onto the target position.

At this time, an energy supplied to a unit area of the target position during radiating the first light is less than that supplied to a unit area of the target position during radiating the second light.

As an example, the first light is radiated with less output than the second light is. Concretely, the light-generation part may be configured to include a light output adjusting part to adjust an output of the light, and the control part may be configured to control the light output adjusting part such that outputs of the first light and the second light are adjusted.

In addition, the optical apparatus may be configured to further include a focusing optical system installed on a traveling path of the light generated in the light-generation part and adjusting a radiated area by the light which radiates onto the target position, wherein the control part may control the focusing optical system such that the first light is radiated onto the radiated area greater than the second light. Herein, the focusing optical system may be configured to include at least one optical member movably installed along the light traveling path, and the optical member may be configured to adjust the radiated area by the light while being moved by the control of the control part.

In addition, the control part may control the radiating time of the first light and the second light in the radiating part, the first light being controlled to be radiated for a shorter period than the second light. Concretely, the optical apparatus may be configured to include at least one shutter installed on a traveling path of the light generated in the light-generation part, and the control part may be configured to control the radiating time of the first light and second light by opening and closing the shutter.

Moreover, the light-generation part may configured to include a first resonator for generating the first light and a second resonator for generating the second light, and the first resonator may be configured to generate light having a wavelength of excellent skin permeability than that of the second resonator. As an example, the first resonator may be configured to generate light of 1064 nm wavelengths, and the second resonator may be configured to generate light of 755 nm wavelengths.

Herein, the control part may control the radiating part such that the first light is radiated, and may control the cooling part such that the cooling gas is sprayed after waiting for time within 100 ms. In addition, the control part may control the cooling part such the cooling gas is sprayed, and may control the radiating part such that the second light is radiated after waiting for 0~100 ms.

Meanwhile, the object of the present invention can be achieved by a method of an optical apparatus for skin treatment, including: radiating first light onto a target position of the skin by driving a light-generation part; spraying cooling gas stored in a storage medium onto the target position; waiting for a predetermined time after spraying the cooling gas; and radiating second light onto the target position by the light-generation part.

In addition, an energy supplied to a unit area of the target position during radiating the first light may be controlled less than that supplied to a unit area of the target position during raidating the second light.

An example, the output light during radiating the first light may be controlled to be radiated less than that during radiating the second light.

In addition, the optical apparatus for skin treatment may further include a focusing optical system to adjust the light-radiated area generated in the light-generation part, wherein the second light during radiating the second light may be controlled to be radiated onto a narrower radiated area than that radiated during radiating the first, by controlling the focusing optical system.

Besides, the radiating time of the first light may be controlled shorter than that of the second light.

Meanwhile, the first light may be generated during radiating the first light using a first resonator of the light-generation part, and the second light may be generated during radiating the second light using a second resonator of the light-generation part, and the first resonator generates light having a wavelength of excellent skin permeability than that of the second resonator. As an example, the first resonator may generate light of 1064 nm wavelengths, and the second resonator may generate light of 755 nm wavelengths.

Advantageous Effects

According to the present invention, since a sufficient amount of thermal energy can be provided to the internal tissue of the skin without damaging to the skin surface, the effect of the treatment of the skin can be improved.

In addition, since the lesions temporarily disappeared due to the cooling of the skin can be minimized; the accuracy of the surgical procedures can be increased.

BEST MODE

Hereinafter, the preferred embodiments of the present invention will be described in detail with reference to the accompanying drawings. In the embodiment to be described below, an apparatus for skin treatment will be described as an example using laser light. However, the preferred embodiment to be described below as one embodiment is not limited thereto, and it is obvious that the present invention can be applied to a variety of light sources other than the laser.

Figure 1:
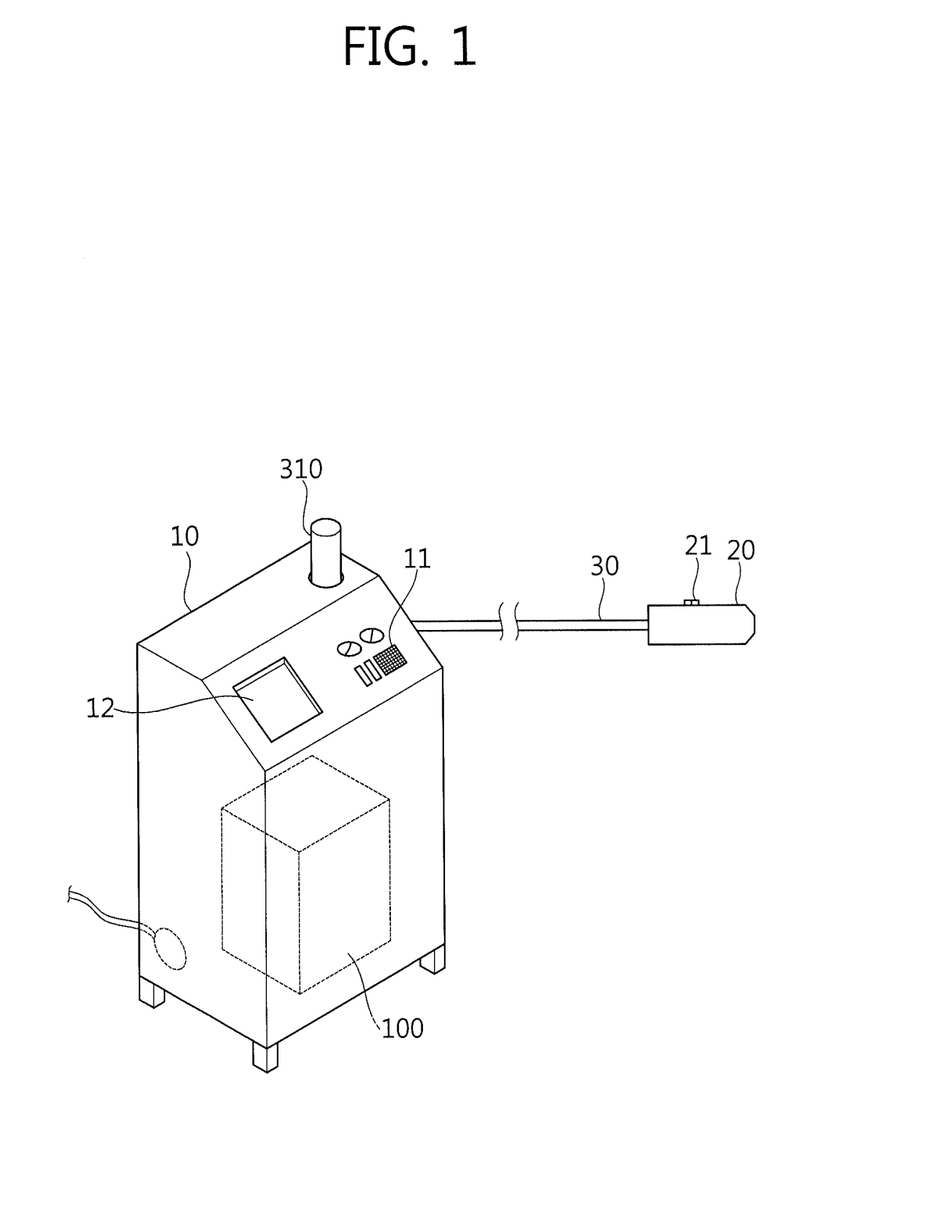
FIG. 1 is a diagram illustrating an optical apparatus for skin treatment according to an embodiment of the present invention.
Figure 2:
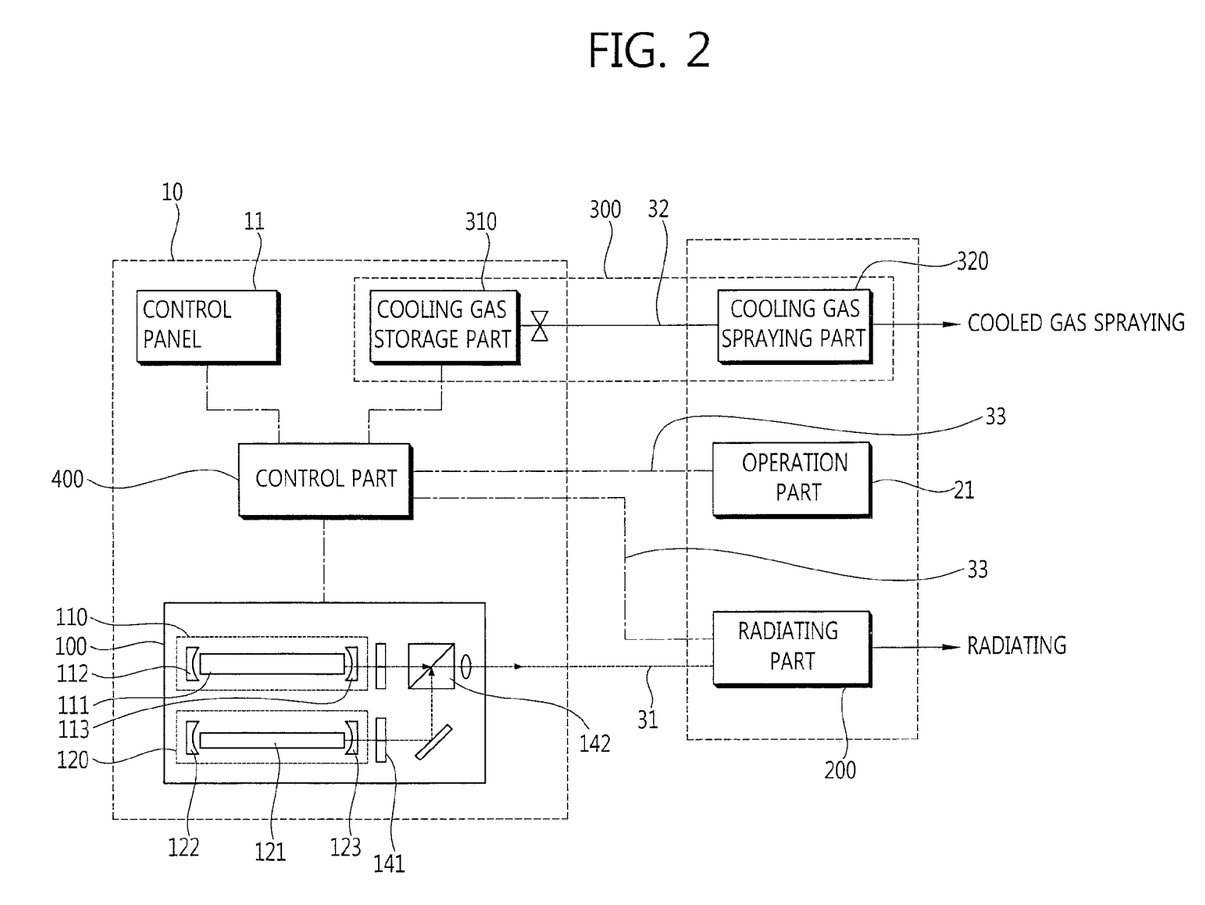
FIG. 2 is a diagram illustrating a connection relationship of a main body and a hand piece of FIG. 1.

FIG. 1 is a diagram illustrating an optical apparatus for skin treatment according to an embodiment of the present invention, and FIG. 2 is a diagram illustrating a connection relationship of a main body and a hand piece of FIG. 1. As shown in FIG. 1, the optical apparatus for skin treatment according to the present invention is configured to include a main body 10, a hand piece 20 and a cable 30 for connecting the main body 10 and hand piece 20.

The main body 10 includes a power supply part to supply power form the outside, and an outer surface of the main body 10 is provided with a control panel 11 to operate surgical contents and a display 12 to display surgical contents to users. And, a light-generation part 100 is provided into the inside of the main body 10 to generate light used in skin treatment, and a cooling gas storage part 310 into which cooling gas for cooling the skin is stored may be installed into the main body 10 as well.

Meanwhile, the hand piece 20 is formed as a hand-catchable structure so as to perform a surgical procedure while the user changes a treatment location. The inside of the hand piece 20 is provided with a radiating part 200 and a cooling gas spraying part 320 to radiate light onto a treatment location and to spray cooling gas. In addition, the outer surface of the hand piece 20 may be formed with an operation part 21 of a button type capable of operating the driving of the hand piece 20 by the user.

In addition, the cable 30 connects the hand piece 20 and the main body 10. In the inside, it may be configured to include an optical fiber 31 forming a light path from the light-generation part 100 to the radiating part 200, a cooling passage 32 for forming a path through which the cooling gas proceeds, and a signal line 33 for transmitting various signals.

Hereinafter, the connection relationship of each component of the main body 10 and the hand piece 20 will be described in detail with reference to FIG. 2.

As shown in FIG. 2, the light-generation part 100 includes at least one resonator 110 and 120. The inside of each of the resonators 110 and 120 is provided with laser mediums 111 and 121, the both ends of the laser medium are provided with optical members such as total reflection mirrors 112 and 122), a shutter 141, partial reflection mirrors 113 and 123, and the like. Thus, light oscillated from the laser medium by an excitation medium such as a flash lamp (not shown) gradually amplifies while being shuttled between the insides of the resonator 110 and 120 and proceeds to form laser light.

In the embodiment of the present invention, the light-generation part 100 is configured to include the first resonator 110 and the second resonator 120, and each of the resonators 110 and 120 includes a laser medium to generate light of different wavelengths. In addition, a shutter 141 for selectively opening and closing the light path and an optical member such as a splitter 142 for light penetration or reflection according to the wavelength characteristic are disposed to selectively provide light having two different wavelengths.

Though the light-generation part 100 is configured as an example using two resonators 110 and 120 in the embodiment of the present invention, it is possible to configure the light-generation part using at least one or three resonators. In addition, though the flash lamp is described as the excitation medium configured for generating a solid-state laser in the embodiment of the present invention, it is of course a variety of configurations may be applied to generate a gas-state laser, a semiconductor laser or the like.

Meanwhile, one end of the light-generation part 100 is connected with the radiating part 200 of the hand piece 20 by a light transmission medium such as the optical fiber 31. Thus, the light generated in the light-generation part 100 is provided to the radiating part 200 of the hand piece 20 along a light path formed by the optical fiber 31. The inside of the radiating part 200 is provided with a focusing optical system 210 consisting of a plurality of optical members such as lenses 211. Accordingly, the light discharged to the end of the optical fiber 31 can be focused and processed to be radiated onto a treatment area.

Meanwhile, a cooling part 300 to cool the skin for treating is configured to include a cooling gas storage part 310 to store the cooling gas and a cooling gas spraying part 320 to spray the cooling gas onto the skin. As shown in FIG. 2, the cooling gas storage part 310 is installed into the main body 10 and the cooling gas spraying part 320 is installed into the hand piece 20 so that they may be connected through the cooling passage 32 of the cable 30.

In the embodiment, the cooling gas may use HFC-134a as an example using cryogen gas to be vaporized at room temperature. The cooling gas is stored in a cooling gas storage part 310 in a high-pressure liquefied state. The cooling gas storage part 310 may be configured as a container structure in which a predetermined amount of cooling gas is stored, and may be removably installed into the outside of the main body 10 so that it can be easily be replaced when the cooling gas is exhausted (see FIG. 1).

The cooling gas storage part 310 is connected with the cooling passage of the inside of the main body 10 when it is coupled to the main body 10. In addition, an opening and closing member such as a solenoid valve is provided on the cooling passage so that the cooling gas may be supplied or blocked to the cooling gas spraying part 320 according to operations of the opening and closing members. Meanwhile, a portion provided with the cooling gas storage part 310 may be provided with a temperature control member such as a heater (not shown) to control the temperature of the cooling gas storage part 310. Accordingly, surface condensation of the cooling gas storage part can be prevented by controlling the surface temperature of the storage part 310 using the temperature control member and the spraying pressure of the cooling gas can be controlled by increasing the inner pressure of the cooling gas storage part 310 as well.

As such, the cooling gas provided from the cooling gas storage part 310 is provided to the hand piece 20 through the cooling passage 32, and sprayed to the treatment location of the skin through the cooling gas spraying part 320 of the hand piece 20. Though in the embodiment of the present invention the cooling gas storage part 310 is configured as a disposable container removably installed into the main body 10 as an example, the present invention is not limited thereto. Besides, it is possible to be configured in such a way that the cooling gas is charged by installing the cooling gas storage part 310 into the main body and to be configured in such a way that the cooling gas storage part 310, not the main body 10, is directly installed into the hand piece 20 as well.

Meanwhile, the optical apparatus for skin treatment according to the embodiment of the present invention includes a control part 400 to control each component. The control part 400 can control operations of each component such as the light-generation part 100, the radiating part 200 and the cooling part 300 according to the terms of the user's input or conditions used in its own memory through the control panel 11. The surgical procedure of a variety of conditions can be performed by controls of the control part 400. Hereinafter, the contents to be controlled by the optical apparatus for skin treatment according to the present invention will be described in detail.

Figure 3:
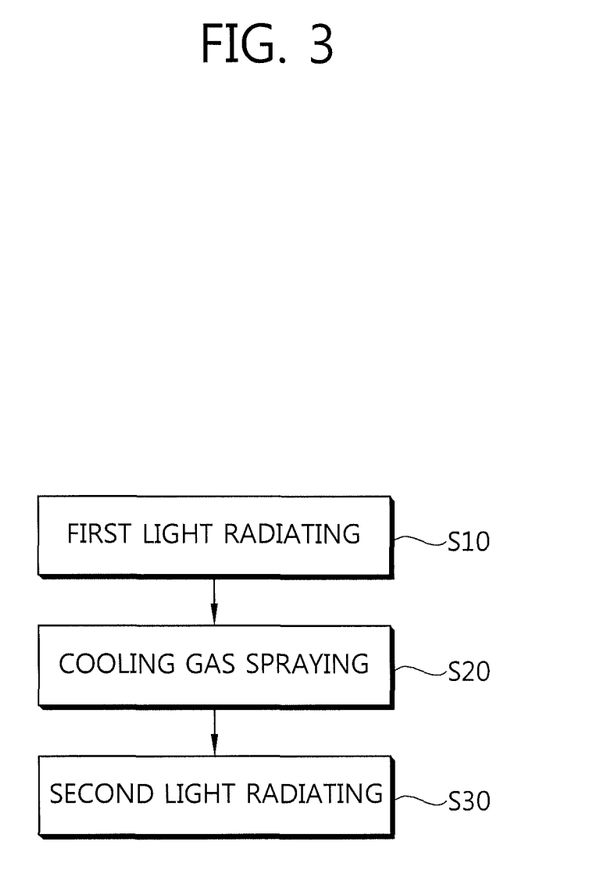
FIG. 3 is a diagram illustrating a control content of an optical apparatus for skin treatment of FIG. 1.

FIG. 3 is a diagram illustrating a control content of an optical apparatus for skin treatment according to the present invention.

As described above, in the optical apparatus for skin treatment of the prior art, the light radiation was performed in a state where the skin is cooled in order to prevent thermal damage to the skin surface. However, though the skin surface is a cooled state, the sufficient thermal energy can not be provided to the internal tissues of the skin since there is a limit to increase the light output.

Therefore, in the optical apparatus for skin treatment according to the present invention, before the skin surface is cooled, the step of radiating the light onto the target position of the skin is preceded (S10). As such, if the first light is radiated onto the skin maintaining a normal body temperature, the skin is pre-heated at the temperature higher than the normal temperature.

Generally, it is may considered that the skin is pre-heated by a thermal conductivity manner in that the skin is in contacted with an object of the higher temperature. However, in this case, the size of the thermal energy provided to the inside of the skin can be linearly reduced as deepened from the skin surface. On the contrary, when the skin is pre-heated in the light illustration manner as in the embodiment, since material absorption characteristics are different from each other according to the light wavelengths material absorption characteristics, it is possible to be pre-heated by the deeper location by providing the thermal energy to the desired location on the inside of the skin.

As such, if the target position of the skin is pre-heated by radiating of the first light, the cooling gas is sprayed by driving the cooling part 300 (S20). In this case, the skin surface is intensively cooled by the heat of vaporization using the sprayed cooling gas while being vaporized at the skin surface. Accordingly, compared to cooling the skin such that the skin surface is in contacted with the object of the low temperature, the temperature of the skin surface can instantaneously be cooled to the cryogenic temperature of less than minus 10, the internal tissues of the skin being maintained in a state holding the thermal energy provided at radiating time of the first light.

If the skin surface is fully cooled in the step, the second light is radiated onto the target position (S30). In this time, the second light can provide the thermal energy to the internal tissue of the skin through the cooled skin. Though the skin surface is a cooled state as described above, there is a limit to increase the output of the second light. However, in the case of the present invention, since the internal tissue of the skin holds the thermal energy supplied at radiating time of the first light, the thermal energy having a sufficient amount needed to treat the skin can be provided to the internal tissue of the skin, together with the thermal energy supplied at radiating time of the second light.

In addition, in the prior art, there was a problem in that some lesions is temporarily disappeared when the skin is cooled, for example, a capillary vessel is contracted and disappeared from the skin surface when the skin is cooled. However, according to the present invention, since the cooling is achieved on the skin surface in a state where the skin is pre-heated, the internal tissue of the skin can be maintained at a temperature higher than the normal body so that some lesions temporarily disappeared due to the cooling of the skin may be minimized.

As such, in the optical apparatus for skin treatment according to the present invention, the control part 400 controls the light-generation part 100, the radiating part 200 and the cooling part 300 such that the step of radiating the first light (S10), the step of spraying the cooling gas (S20) and the step of radiating the second light (S30) can be proceed sequentially.

However, since the step of radiating the second light (S30) may be proceed in a state that the skin surface is cooled and the step of radiating the first light (S10) may be proceed in a state the surface is not cooled, if the first light provides the thermal energy excessively, it may cause damage to the skin surface.

Thus, it is desirable that the first light and the second light are radiated such that an energy supplied by the first light to an unit area of the skin during radiating the first light is less than that supplied by the second light to an unit area of the skin during radiating the second light. Accordingly, the thermal energy can be provided by a degree that does not scald the skin surface maintaining the normal temperature when the first light is radiated, and the thermal energy having a sufficient amount needed to treat the skin can be provided when the second light is radiated. The step of radiating the first light and the step of radiating the second light can be variously implemented by differently adjusting a radiating light output, a light-radiated area, a light radiating time or the like, respectively. With respect to this, it will be described in detail below.

Figure 4:
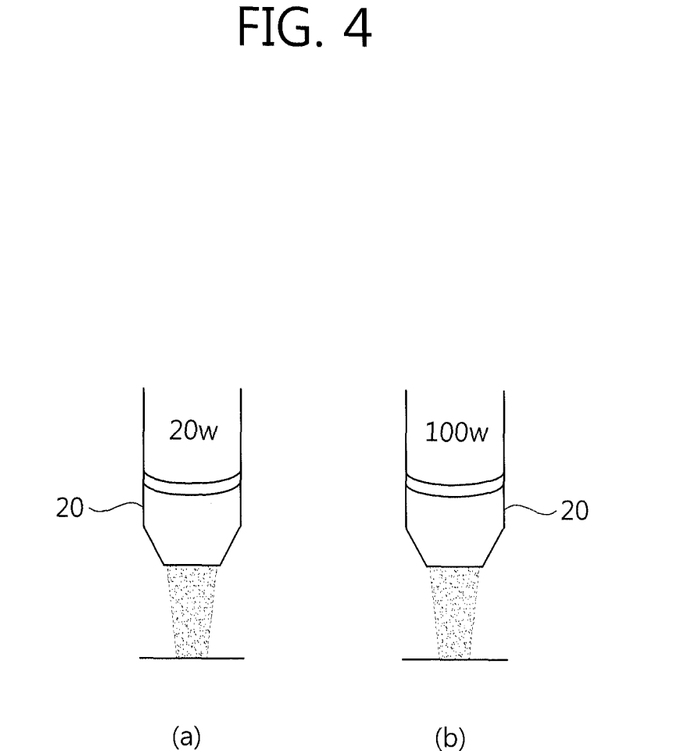
FIGS. 4 to 6 are diagrams illustrating configuration examples of a first light and a second light in FIG. 3.

Firstly, in the step of radiating the first light (S10) and the step of radiating the second light (S30), the light outputs to be radiated through the radiating part 200 can be differently controlled. Herein, the light output may be controlled in a variety of ways. As an example, the light output can be controlled by adjusting the amount of current supplied to the flash lamp to excite the laser medium in the light-generation part 100. Thus, the control part controls the light-generation part 100, the first light can be radiated as a relatively small output (for example, 20 W, see FIG. 4(a)) in the step of radiating the first light (S10), and the second light can be radiated as an output (for example, 100 W, see FIG. 4(b)) greater than at the time of radiating the first light in the step of radiating the second light (S30). If the first light and the second light having the same wavelength is radiated onto the same radiated area during the same time, the first light having the relatively small output can provide a small amount of the thermal energy compared to the second light to the skin surface.

Figure 5:
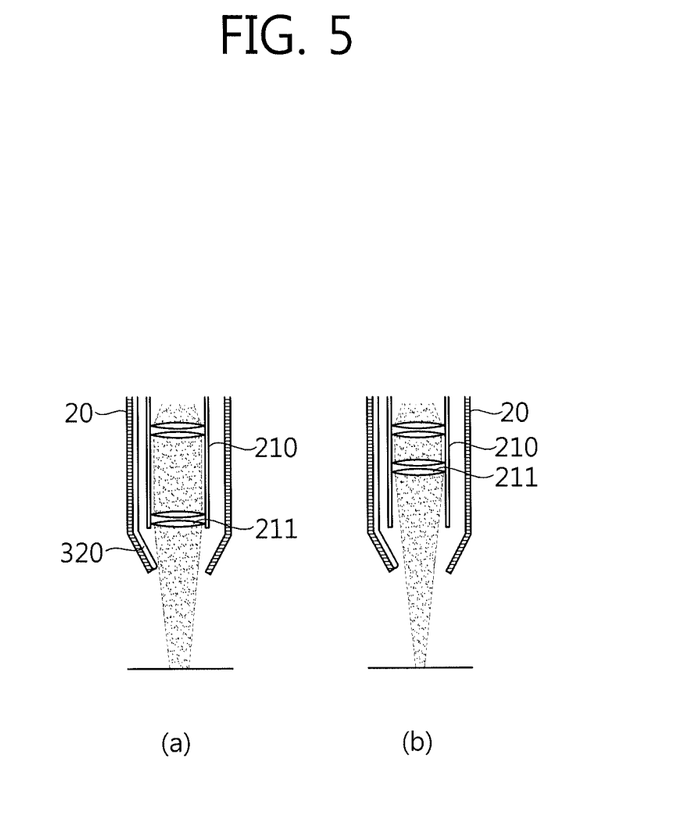

In addition, in the step of radiating the first light (S10) and the step of radiating the second light (S30), an amount of energy to be transmitted to the skin can be controlled by adjusting the light-radiated area in the each step. In the present embodiment, as shown in FIG. 5, the radiating part 200 of the hand piece 20 is configured to include a focusing optical system 210 for focusing and radiating the light transmitted from an optical fiber. The focusing optical system 210 includes at least one optical member such as a lens 211 to control the size of the light-radiated area by changing locations of the optical members consisting of the focusing optical system 210. At this time, in the light having the same wavelength and radiated onto the same radiated area during the same time, the energy supplied to the unit area is reduced as the radiated area is greater. Accordingly, in the step of radiating the first light (S10), the amount of the thermal energy supplied to the target position per an unit area can be reduced by radiating the light onto the greater radiated area compared to the step of radiating the second light (S30) (see FIG. 5). In this case, as the first light is radiated onto the greater radiated area, it is possible to obtain the effect in that the thermal energy can be supplied to the deeper location of the skin as well.

Besides, it is possible to control an amount of thermal energy to be transmitted by adjusting a time that light is radiated. As the light radiating time is shorter, the amount of thermal energy applied to the skin is smaller. Accordingly, the time for radiating the first light can be controlled shorter than the time that the second light is radiated to prevent thermal damage generated in the pre-heating process.

As such, the control part differently controls at least one conditions of the light output, the radiated area and the radiating time when the first light and the second light are radiated. Thus, the skin tissue is pre-heated without damaging the skin surface during radiating the first light, and the sufficient thermal energy is provided to the cooled skin during radiating the second light.

In this time, the treatment for skin lesion is mainly performed by the second light, and the internal tissue of the skin is mainly pre-heated by the first light, rather than the treatment for the skin directly. Here, the first light and the second light may use the same light wavelengths, but it is preferable to use different light wavelengths, taking into account functions performed in each step by the first light and the second light.

Figure 6:
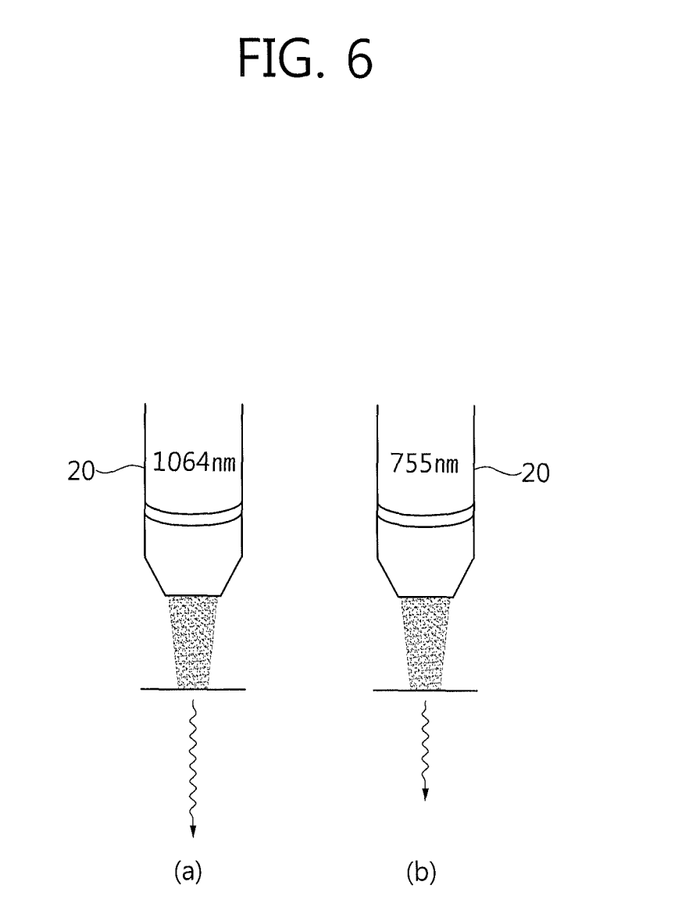

According to the present embodiment, the light-generation part includes a first resonator 110 to generate the first light and a second resonator 120 to generate the second light (see FIG. 2). Herein, the second resonator 120 is configured to generate the effective light wavelengths in the treatment of the skin lesion. In addition, the first resonator 110 is configured to generate the light wavelengths having the excellent skin permeability compared to the second resonator 120 to enhance the pre-heating effect of the skin when the first light is radiated. As an example, the first resonator 110 is configured to include Nd:YAG (Yttrium Aluminum Garnet with Neodymium) mediums and the second resonator 120 are configured to include Alexandrite (chrysoberyl crystal with chromium mediums. Thus, when the first light is radiated, the skin can be pre-heated by radiating 1064 nm light wavelengths having the excellent skin permeability generated from the first resonator 110 (see FIG. 6(a)). In addition, when the second light is radiated, the skin lesion can be treated by 755 nm light wavelengths generated from the second resonator 120 (see FIG. 6(b)).

As described above, the optical apparatus for skin treatment according to the present invention can be operated such that the second light for treatment of the skin lesion may be radiated after radiating the first light for pre-heating of the skin and spraying the cooling gas by the control of the control part 400. At this time, the user can instruct the control part 400 to perform operations through the control panel 11 or the operation part 21, and the control part 400 may sequentially process the above-mentioned three steps as a set of operations when the instruction of the user has been input.

Figure 7:
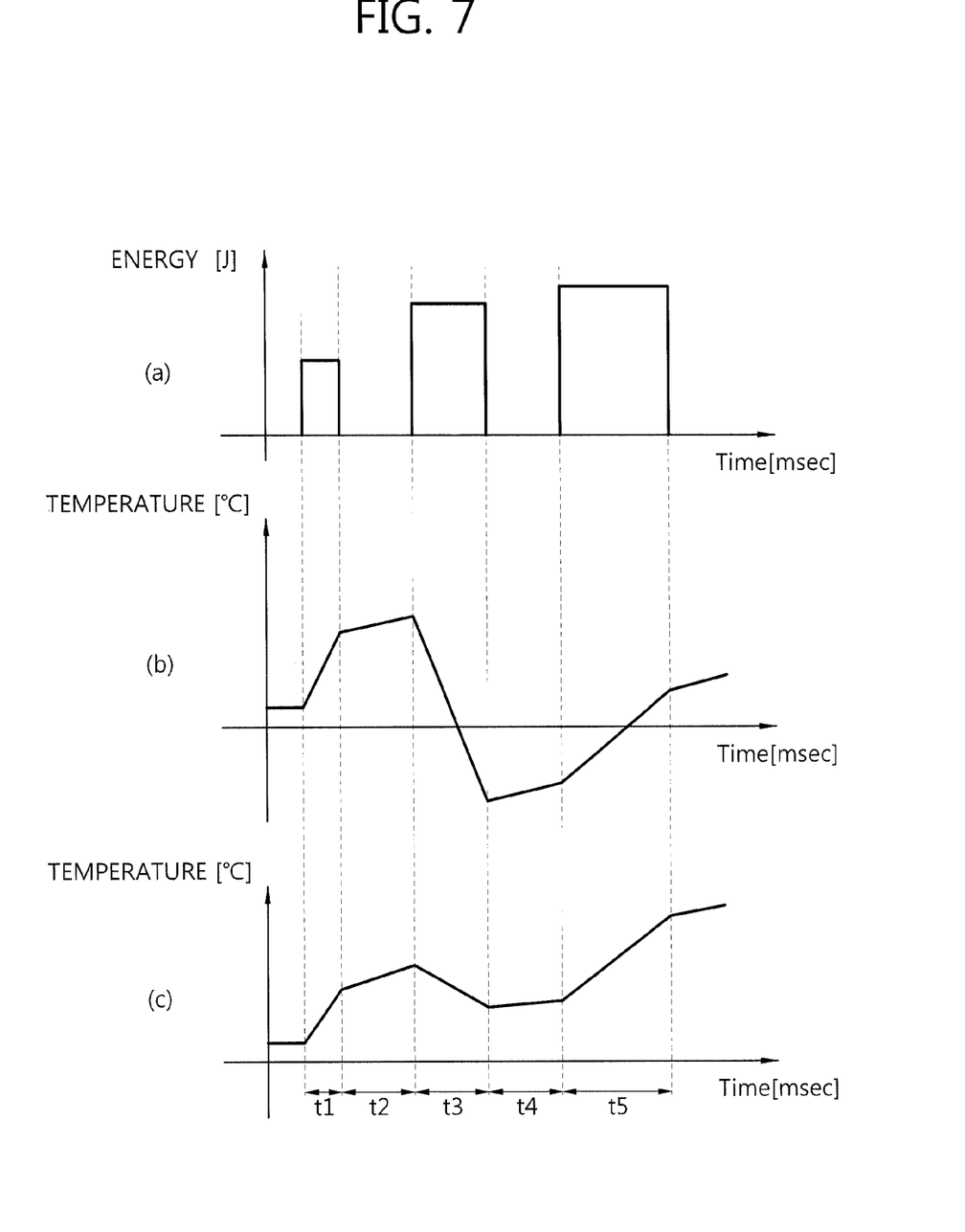
FIG. 7 is a graph showing temperature changes of the skin when controlling an optical apparatus for skin treatment according to a sequence of FIG. 3.

FIG. 7 is a graph showing temperature changes of the skin when controlling an optical apparatus for skin treatment according to a sequence of FIG. 3, wherein FIG. 7(b) shows a temperature of a skin surface, and FIG. 7(c) shows a temperature of an internal tissue of the skin. Hereinafter, the temperature changes of the skin surface and the internal tissue of the skin will be described with reference to FIG. 7 when treating the skin using the embodiment of the present invention.

First of all, the first light having 1064 nm wavelengths may be raidated onto the target position of the skin maintained at a normal temperature during the time t1. At this time, it is desirable to set the radiated area and the radiating time according to the light output such that the temperature of the skin surface may be not increased by 50 above while being radiating the first light. Specifically, the first light can be radiated onto 50 mm² or more radiated areas within the range from 1 ms to 1 s.

As described above, as the first light is radiated, the surface temperature of the target position is gradually increased (see FIG. 7), and it is pre-heated while the temperature of the internal tissue of the skin is increased as well (see FIG. 7).

Meanwhile, even when radiating of the first light has completed, the temperatures of the skin surface and the internal tissue of the skin will be decreased after being continuously increased for a predetermined time. Thus, after the first light has radiated, a standby state can be maintained during the time t2 until the temperature of the skin is increased enough. At this time, the standby state can be maintained less than 10 to 100 ms, and it is also possible to set to progress the immediately following step, without progressing the standby state, depending on the user's decision.

As described above, if the target position of the skin is pre-heated by radiating of the first light, the skin surface is cooled by spraying the cooling gas onto the target position. The cooling gas spray time t3 may be controlled in the range from 10 ms to 300 ms.

In this case, as shown in FIG. 7, the skin surface of the target position is rapidly cooled to below minus 10 degrees by spraying the cooling gas (see FIG. 7(*a*)). On the contrary, the internal tissue of the skin is largely unaffected by spraying the cooling gas and the pre-heated state is maintained at a temperature greater than the normal temperature (see FIG. 7(*b*)).

If the cooling gas has sprayed, after the standby time t4 has elapsed during the range from 10 ms to 100 ms, the second light is radiated onto the target position. As described above, the second light has 755 nm wavelengths, and the light output, the radiating time and the radiated area can be set according to the skin lesion.

The thermal energy is provided to the skin surface of the target position and the internal tissue of the skin by radiating the second light, thereby increasing the temperature. At this time, the inside of the target position is additionally provided with the thermal energy in a pre-heated state by the first light, the temperature being increased in higher temperature compared to the prior art.

As such, according to the present invention, since the skin surface is cooled in a state where the target position is primarily pre-heated by radiating the light and the treatment is performed by secondarily radiating the light, it is possible to provide the sufficient thermal energy required for the treatment without damaging of the skin surface.

Although the step of radiating the first light, the step of spraying the cooling gas, and the step of radiating the second light are configured to be controlled as a set of operations according to the present embodiment as an example, the present invention is not limited thereto. Besides, it is also possible to perform the step of radiating the light in several times repeatedly in a way that the second light is radiated and then, the cooling gas is again sprayed. In addition, by modifying the sequences based on the lesions, it can be applied to a variety of treatment fields such as skin, capillary vessel or the like.

The invention claimed is:

1. An optical apparatus for skin treatment, comprising:
    a first laser source configured to emit a first pulsed laser beam at a first wavelength;
    a second laser source configured to emit a second pulsed laser beam at a second wavelength, the second laser source comprising an Alexandrite medium, wherein an optical penetration depth of the first wavelength in skin is higher than a respective optical penetration depth of the second wavelength;
    a radiating part for radiating the first laser beam and the second laser beam onto a surface of a target portion of the skin to be treated;
    a focusing optical system configured to focus and adjust a spot size of the first laser beam and the second laser beam;
    a cooling part for spraying cooling gas onto the surface of the target portion of the skin to cool the surface of the target portion of the skin; and
    a control part configured to control the first laser source, the second laser source, and the cooling part, in a sequence wherein:
        first, the radiating part radiates a pulse of the first laser beam onto the target portion of the skin for preheating the surface of the target portion of the skin to a temperature $T_1$, and the focusing optical system focuses the first laser beam to a first spot size;
        second, waiting a first period of time of 10 to 100 ms, immediately after radiating the first laser beam;
        third, after the first waiting period, the cooling part sprays the cooling gas onto the target portion of the skin and cools the surface of the target portion of the skin without cooling an internal tissue of the target portion of the skin that remains at a temperature higher than that of the internal tissue prior to radiating the pulse of the first laser beam; and
        fourth, waiting for a second time ranging from 10 to 100 ms after the cooling part sprays the target portion; and
        fifth, the second laser source radiates a pulse of the second laser beam with a power greater than that of the pulse of the first laser beam onto the target portion of the skin for treating the target portion at a temperature $T_2$ that is higher than $T_1$, and the focusing optical system focuses the first laser beam to a second spot size that is smaller than the first spot size.

2. The optical apparatus of claim 1, wherein the first laser source is an ND:YAG laser.

3. The optical apparatus of claim 2, wherein the first wavelength is at 1064 nm.

4. The optical apparatus of claim 1, wherein the second wavelength is at 755 nm.

5. The optical apparatus of claim 1, wherein the cooling part has a solenoid valve.

6. The optical apparatus of claim 1, wherein the cooling part has a storage part for the cooling gas.

7. The optical apparatus of claim 1, wherein the focusing optical system includes at least one optical member arranged to slide along an optical path of the first and second laser beams.

8. The optical apparatus of claim 1, wherein the control part controls radiating time of the first laser beam and the second laser beam, the first laser beam being controlled to be radiated for a shorter period than the second laser beam.

9. The optical apparatus of claim 8, wherein a shutter is arranged in an optical path of the first and second laser beams, wherein the control part controls the radiating time of the first and second laser beams by opening and closing the shutter.

10. The optical apparatus of claim 1, wherein the first and second light sources are integrated.

11. The optical apparatus of claim 1, wherein the first wavelength is at 1064 nm and the second wavelength is at 755 nm.

12. The optical apparatus of claim 1, wherein the radiating part is a handpiece.

* * * * *